(12) United States Patent
Ciliberto et al.

(10) Patent No.: US 6,706,261 B1
(45) Date of Patent: Mar. 16, 2004

(54) COMPOSITIONS AND METHODS COMPRISING IMMUNOGENIC MUTEINS OF INTERLEUKIN-6

(75) Inventors: Gennaro Ciliberto, Rome (IT); Rocco Savino, Pomezia (IT); Riccardo Cortese, Rome (IT)

(73) Assignee: Istituto di Ricerche di Biologia Molecolare P. Angeletti S.p.A.

(*) Notice: Subject to any disclaimer, the term of this patent is extended or adjusted under 35 U.S.C. 154(b) by 0 days.

(21) Appl. No.: 09/559,950

(22) Filed: Apr. 27, 2000

Related U.S. Application Data (63) Continuation of application No. 09/029,657, filed as application No. PCT/IT96/00164 on Aug. 22, 1996, now abandoned.

(30) Foreign Application Priority Data

Sep. 1, 1995 (IT) .......................... RM95A0589

(51) Int. Cl.[7] .................. C07K 14/54; C12P 21/02; A61K 38/20
(52) U.S. Cl. .................. 424/85.2; 435/69.1; 514/2; 514/8; 530/351
(58) Field of Search .................. 530/351; 435/69.1; 424/85.2; 514/2, 8

(56) References Cited

FOREIGN PATENT DOCUMENTS

| | | |
|---|---|---|
| WO | WO 92/22577 | 12/1992 |
| WO | WO 94/02512 | 2/1994 |
| WO | WO 94/11402 | 5/1994 |
| WO | WO 95/00852 | 1/1995 |
| WO | WO 97/10338 | 3/1997 |

OTHER PUBLICATIONS

De Hon e t al. Development of an IL–6 receptor antagonist that inhibits IL–6 dependent growth of human myeloma cell. Journal o Experimental medicine. Dec. 1994. vol. 180, pp. 2395–2400.*
Blood 87 (11). 1996. 4510–4519, XP000612195. Sporeno E. et al., "Human interleukin–6 receptor super–antagonists with high potency and wide spectrum on multiple myeloma cells."
Brakenhoff, Just P.J. et al. "Development of a Human Interleukin–6 Receptor Antagonist." *The Journal of Biological Chemistry*. (1994) 269(1): 86–93.
Brakenhoff, Just P.J. et al. "Structure–Function Analysis of Human IL–6: Epitope Mapping of Neutralizing Monoclonal Antibodies with Amino–and Carboxyl–Terminal Deletion Mutants." *The Journal of Immunology*. (1990) 145(2): 561–568.

* cited by examiner

*Primary Examiner*—Prema Mertz
*Assistant Examiner*—Fozia Hamud
(74) *Attorney, Agent, or Firm*—Joseph Fischer; Beusse, Brownlee, Wolter, Mora & Maire, P.A.

(57) ABSTRACT

Cytokines, including muteins thereof, which are biologically inactive in humans but remain immunogenic, are used in pharmaceutical compositions to promote a neutralizing immune response against native cytokines when administered to a subject in need thereof to treat homeostatic disorders and disorders associated with an overproduction of cytokines.

12 Claims, 8 Drawing Sheets

Antibodies elicited by wild type hIL-6 formulated in aluminum hydroxide and injected I.P. are not neutralizing % of rhIL-6 bioactivity vs. Serum dilutions Legend: 35, 51, 53, 60, 75, 85, 87, 90, 93, 99

FIG.6a

FIG.6b Antibodies elicited by wild type hIL-6 formulated in aluminum hydroxide and injected I.P. are neutralizing

SEQUENCE LISTING

```
<160> NUMBER OF SEQ ID NOS: 1

<210> SEQ ID NO 1
<211> LENGTH: 184
<212> TYPE: PRT
<213> ORGANISM: Artificial Sequence
<220> FEATURE:
<223> OTHER INFORMATION: Mutant of human wild type Interleukin-6
<220> FEATURE:
<221> NAME/KEY: MUTAGEN
<222> LOCATION: (31)..(31)
<223> OTHER INFORMATION: mutation Tyr/Asp from human IL-6 wild type
```

-continued

```
      sequence
<220> FEATURE:
<221> NAME/KEY: MUTAGEN
<222> LOCATION: (35)..(35)
<223> OTHER INFORMATION: mutation Gly/Phe from human IL-6 wild type
      sequence
<220> FEATURE:
<221> NAME/KEY: MUTAGEN
<222> LOCATION: (118)..(118)
<223> OTHER INFORMATION: mutation Ser/Arg from human IL-6 wild type
      sequence
<220> FEATURE:
<221> NAME/KEY: MUTAGEN
<222> LOCATION: (121)..(121)
<223> OTHER INFORMATION: mutation Val/Asp from human IL-6 wild type
      sequence
<220> FEATURE:
<221> NAME/KEY: MUTAGEN
<222> LOCATION: (175)..(175)
<223> OTHER INFORMATION: mutation Gln/Ile from human IL-6 wild type
      sequence
<220> FEATURE:
<221> NAME/KEY: MUTAGEN
<222> LOCATION: (176)..(176)
<223> OTHER INFORMATION: mutation Ser/Arg from human IL-6 wild type
      sequence
<220> FEATURE:
<221> NAME/KEY: MUTAGEN
<222> LOCATION: (183)..(183)
<223> OTHER INFORMATION: mutation Gln/Ala from human IL-6 wild type
      sequence

<400> SEQUENCE: 1

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
        35                  40                  45

Met Cys Glu Ser Ser Lys Glu Ala Leu Ala Glu Asn Asn Leu Asn Leu
    50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
            100                 105                 110

Arg Ala Val Gln Met Arg Thr Lys Asp Leu Ile Gln Phe Leu Gln Lys
        115                 120                 125

Lys Ala Lys Asn Leu Asp Ala Ile Thr Thr Pro Asp Pro Thr Thr Asn
    130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Ile Arg
                165                 170                 175

Ser Leu Arg Ala Leu Arg Ala Met
            180
```

COMPOSITIONS AND METHODS COMPRISING IMMUNOGENIC MUTEINS OF INTERLEUKIN-6

CROSS-REFERENCE TO RELATED APPLICATIONS

This application is a continuation of U.S. patent application Ser. No. 09/029,657, filed Feb. 27, 1998, now abandoned which was a section 371 for PCT/IT96/00164, filed Aug. 22, 1996, now abandoned.

The present invention relates to the use of muteins of a specific wild-type cytokine, that are also receptor antagonists of the latter, as immunogens to elicit antibodies against the wild-type cytokine, said antibodies being capable of neutralising the biological activity of the wild-type cytokine in diseases caused by an excessive production of the latter.

It is a known fact, for example, that human interleukin 6 (hIL-6) is a polypeptide of 184 aminoacids belonging to the class of helical cytokines. Interleukin 6 is a multi-functional cytokine produced by various cell types. It acts as a differentiation and growth factor on cells of various types, for example the cells of the immune system, hepatocytes, kidney cells, haematopoietic stam cells, keratinocytes and neurons. However, excessive production of hIL-6 is causes a number of diseases, such as chronic auto-immune disorders, systemic lupus erythematosus, myeloma/plasmacytoma, post-menopausal osteoporosis and cancer cachexy.

There is thus a need in this specific sector to counteract the excessive production of a wild-type cytokine in general, and of hIL-6 in particular, both in terms of prevention and of cure.

The use of the present invention enables this need to be satisfied, offering at the same time other advantages which will become clear from the following.

A subject of the present invention is in fact the use of mutants of a wild-type cytokine for the preparation of pharmaceutical compounds for the treatment or prevention or diseases caused by an overproduction of this specific wild-type cytokine.

A further subject of the present invention are pharmaceutical compounds for treatment of diseases caused by the excessive production of a wild-type cytokine, or vaccines for the prevention of said diseases containing as an active principle at least one mutant of that wild-type cytokine.

The pharmaceutical compounds according to the present invention may be formulated according to known methods, which requires for example the presence of a pharmaceutically acceptable vehicle. Examples of these vehicles and methods of formulation can be found in Remington's Pharmaceutical Sciences. To form a pharmaceutically acceptable compound suitable for effective administration, these compounds must contain an effective amount of the active principle according to the present invention. The pharmaceutical compounds of the present invention are administered to an individual in amounts adequate to the disease, the weight, the sex and the age of the individual in question. Other factors include the method of administration. The pharmaceutical compounds according to the invention may be administered in a wide range of manners, for example subcutaneously, topically, orally and by intramuscular injection.

The pharmaceutical compounds according to the present invention, containing as an active ingredient at least one mutein of a wild-type cytokine, may be administered at therapeutic doses in a wide variety of forms, in conventional administration vehicles.

For example, they can be administered in doses to be taken orally in the form of tablets, capsules, pills, powders, granules, elixirs, ointments, solutions, suspensions, syrups and emulsions, or by injection. In the same way, these compounds according to the invention may be administered endovenously, intraperitoneally, subcutaneously, topically with or without occlusion, or intramuscularly. All the above formes of dosage are well known to those skilled in the pharmaceutical field. In any case an effective, but non toxic amount of the active principle according to the invention must be used.

The daily dose of this active principle may vary within a wide range of between 0.01 to 1000 mg per adult/per day. An effective amount of the active principle according to the invention is usually provided at a dosage of between approximately 0.001 mg/kg and approximately 100 mg/kg of body weight per day.

According to the present invention, the active principle, which is made up of muteins of a specific wild-type cytokine, may be administered typically in a mixture with suitable diluents, excipients or pharmaceutical vehicles (generally referred to by the general term "vehicles") suitably selected so as to bear in mind the form of administration desired.

The preparation of vaccines according to the present invention is known to persons skilled in this field. Typically, these vaccines are prepared in an injectable form, either, as solution or as suspensions. The preparation can be emulsionated, or the active principle can be incapsulated in lyposomes. The active immungenic ingredient is often mixed with pharmaceutically acceptable excipients that are compatible with the active ingredient. Suitable excipients are, for example, water, dextrose, glycerol, ethanol or the like and combinations thereof. Furthermore, if desired, the vaccine may contain small amounts of additional substances, such as, for example, wetting or emulsionating agents, pH buffering agents, and/or adjuvants to increase the effectiveness of the vaccine.

The vaccines according to the invention are preferably administered parenterally, for example by means of either intramuscular or subcutaneous injection. Other formulations suitable for other methods of administration include suppositories and oral formulations. These compounds contain from 10 to 95% of active ingredient, preferably between 25 and 70%.

Up to this point a general description has been given of the present invention. With the aid of the following examples a more detailed description will now be given, indicating specific situations that can be referred to the present invention, and aimed at giving a clearer understanding of the aims, characteristics, advantages and possible applications thereof.

All publications and applications, cited previously or herein, are hereby incorporated by reference.

EXAMPLE 1

Immunisation of NSE/hIL-6 Transgenic Mice, With Immune Tollerance for hIL-6, Using hIL-6 and Sant1

The NSE/hIL-6 transgenic mice have integrated into their genome the cDNA of human interleukin 6, under the control of the rat neuro-specific enolase gene promote.

The theory of tollerance was verified by attempting to immunize the above mentioned NSE/hIL-6 transgenic mice (a group of five mice) with recombinant human IL-6; as a control, siblings born in the same litter, but without the transgene were used. A group of five NSE/hIL-6 transgenic mice was also immunised with a mutant form of IL-6, called Sant1 (which does not have residual biological activity on human cells and behaves as an h-IL 6 receptor antagonist), which contained the seven mutations indicated below: Tyr 31 Asp, Gly 35 Phe, Ser 118 Arg, Val 121 Asp, Gln 175 Ile, Ser 176 Arg, Gln 183 Ala. In this case also five siblings from the same litter but without the transgene were as controls. The immunisation protocol was as follows: at time zero a sample of blood (pre-immune sample) was taken in sequence from each animal, both transgenic and non, and then each animal was immunised intraperitoneally (IP) with 100 µg of antigen (wt hIL-6 or Sant1, according to the group of mice) in the presence of Complete Freund Adjuvant (CFA). Ten days after the first immunization, a blood sample was taken (sample 1). Twenty days after first immunization a second immunization was carried out (first booster), again using 100 µg of antigen, in the presence of Incomplete Freund's Adjuvant (IFA), followed ten days later (30 days from first immunization) by a second blood sample (sample 2). Finally, fourty days after the first immunization a third immunization was carried out (second booster) again using 100 µg of antigen, in the presence of IFA, followed ten days later (50 days from first immunization) by the third blood sample (sample 3). The corresponding serum was prepared from each of the blood samples, according to the state of the art.

At this point the "ELISA" method (Enzyme Linked ImmunoSorbent Assay) was used to test whether or not antibodies directed against the antigen used for immunization were present in the serum obtained from the second and third samples. To do this, the same antigen used for immunization was bound in a non co-valent manner to the bottom of the wells in culture plates specially produced for this type of experiment (ELISA plates). Immobilisation of the antigen took place by incubating 100 µl of a solution of antigen dissolved at 10 µl/ml in 1×PBS for 14 hours at room temperature in each of the wells to be coated (an operation termed "coating"). After immobilisation of the antigen, the plastic in the wells was coated with proteins, incubating a solution of 0.8% BSA (Bovine Serum Albumin) in 1×PBS for 4 hours at room temperature in each of the wells (an operation termed "blocking"). After removal of the "blocking" solution, 100 µl of each serum, suitably diluted, were incubated singly in each well for 90 minutes at room temperature: during this stage, if there are in the serum any antibodies for the antigen immobilised on the bottom of the well, these will bind the antigen itself, and will in turn be bound to the bottom of the well. After the 90 minute incubation period, the serums were removed from the wells and, after adequate washing, 100 µl of 0.8% BSA in 1×PBS containing rabbit antibodies directed against mouse antibodies were added to each well, and incubation was continued for 50 minutes at room temperature. During this stage, if mouse antibodies have recognised and bound the antigen immobilised on the bottom of the well, these mouse antibodies will be recognised and bound by the rabbit antibodies, which will thus in turn be immobilised on the bottom of the well. Furthermore, the rabbit antibodies directed against mouse antibodies (used diluted at a ratio of 1:100 in PBS/BSA for the above mentioned experiment), which are produced and distributed by the company DAKO, are covalently linked to an enzyme, horseradish peroxidase. After the 50 minutes of incubation, the solution containing rabbit antibodies was removed, and the wells were adequately washed. At this point, 100 µl of a solution containing a substrate (TMB: 3,-3',-5,-5'-tetramethyl-benzydine-dichloride) for horseradish peroxidase were added to each well. The enzyme converts the substrate into a product that absorbs visible light at 450 nanometers; thus the amount of conversion can be calculated by spectrophotometric measurement of the light absorbtion at 450 nm in each single well, using an ELISA reader. If the experiment is carried out correctly, the absorbance (that is to say the amount of light absorbed) is proportional to the amount of enzyme, which is in turn proportional to the amount of rabbit antibody, which is in turn proportional to the amount of mouse antibody directed against the antigen originally present in the serum. Thus, the measurement of the absorbance gives an estimate of the amount of mouse antibody directed against the antigen present in the serum. This is true if the mouse antibody against the antigen is the factor limiting the chain of reactions described above. Thus, to obtain the appropriate conditions, it is advisable to carry out a series of dilutions (from 1:33 to 1:8100) for each serum to be examined, so that, for each serum there will be certain dilutions in which the amount of mouse antibody for the antigen used for immunization will be sufficiently high to be measured with precision, but not so high as to saturate the system.

Figure 1A:
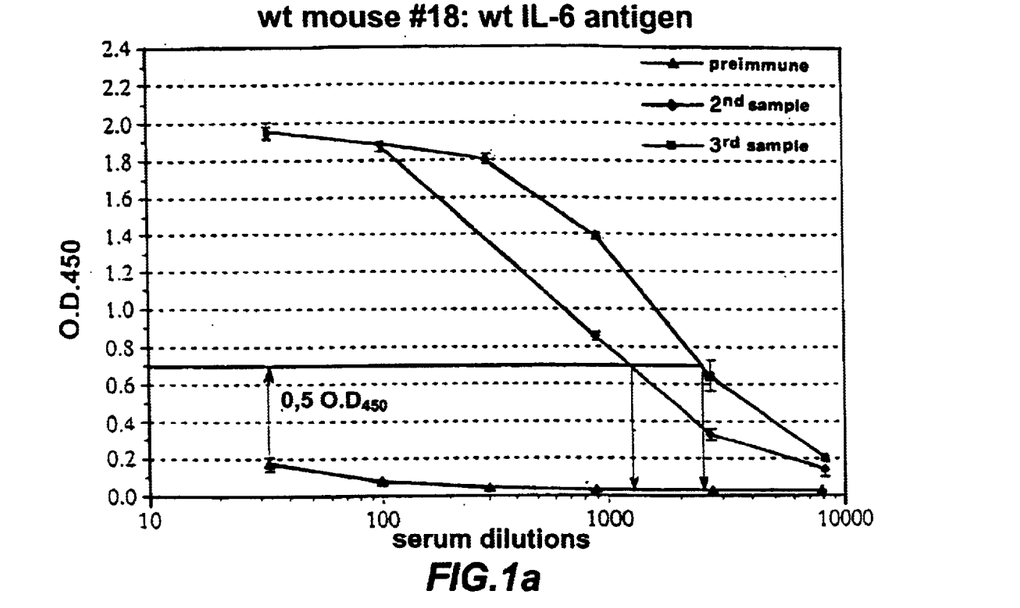
FIGS. 1a and 1b show the results of the experiment of immunisation of normal and NSE/hIL-6 transgenic mice with wild-type hIL-6.
Figure 1B:
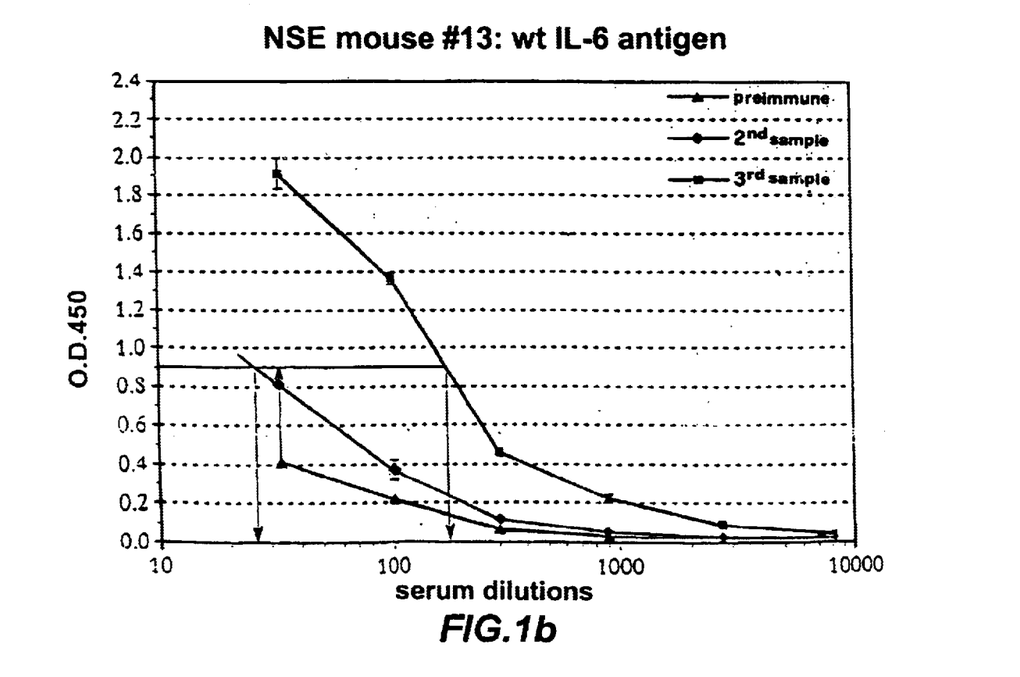

The results of the wild-type IL-6 (wtIL-6) immunization experiment are illustrated in FIGS. 1a and 1b for a typical normal mouse and for a typical NSE/hIL-6 transgenic mouse. As can be seen from FIG. 1a, the normal mouse has developed a large amount of anti-wtIL-6 antibodies, so much so that it is possible to detect a signal even when the serum is diluted to 1:8100. Vice versa, as can be seen from FIG. 1b, the transgenic mouse has developed a much lower amount of antibodies: in fact the signal ceases when the serum from the second sample is diluted at a ratio of 1:300 and when the serum from the third sample is diluted at a ratio of 1:2700. To carry out objective measurements that are comparable for all animals, the dilution of serum that gives a reading of 0.5 O.D.$_{450}$ above the highest reading of the pre-immune serum from the same animal has been conventionally termed "titer". FIGS. 1a and 1b show how the titer of the second and third samples are calculated for normal mice and for the NSE/hIL-6 transgenic mice, respectively.

Figure 2A:
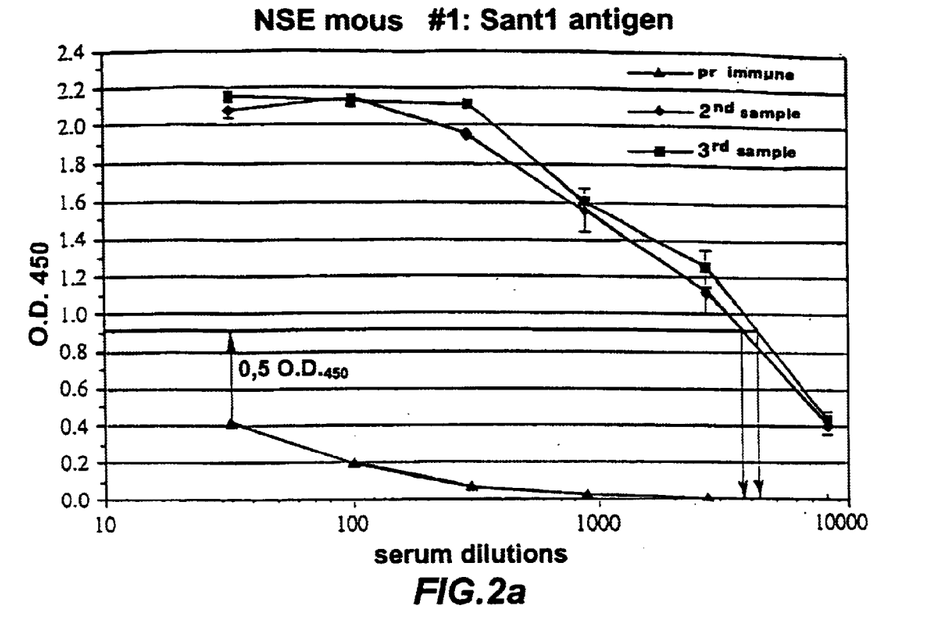
FIGS. 2a and 2b show the results of the experiment of immunisation with the mutant form, briefly indicated as Sant1 (containing the mutations Tyr 31 Asp, Gly 35 Phe, Ser 118 Arg, Val 121 Asp, Gln 175 Ile, Ser 176 Arg, Gln 183 Ala and being an antagonist of hIL-6) in normal and in NSE/hIL-6 transgenic mice.
Figure 2B:
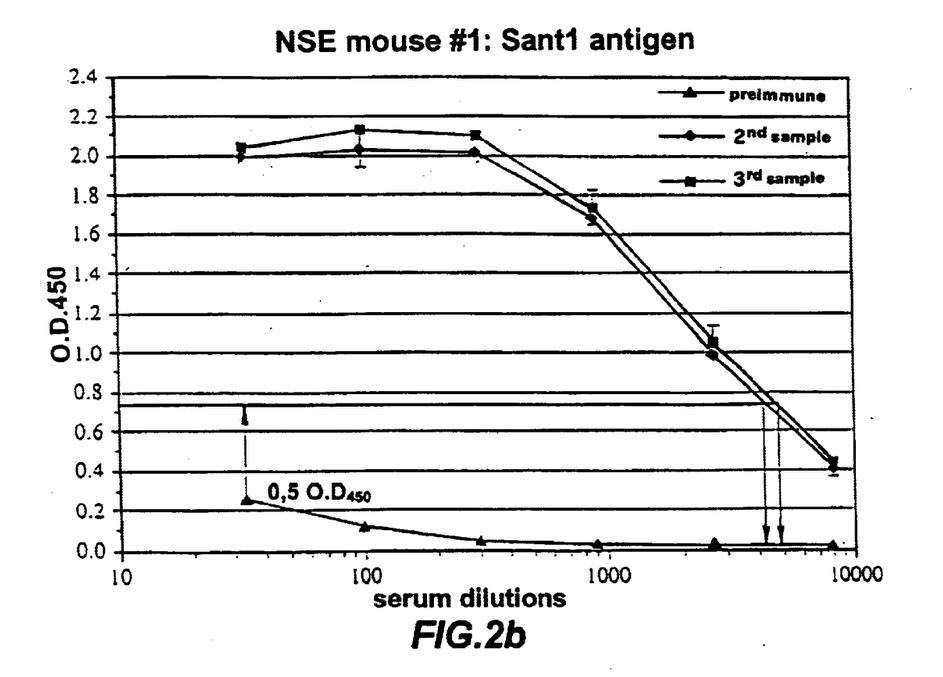
Figure 3:
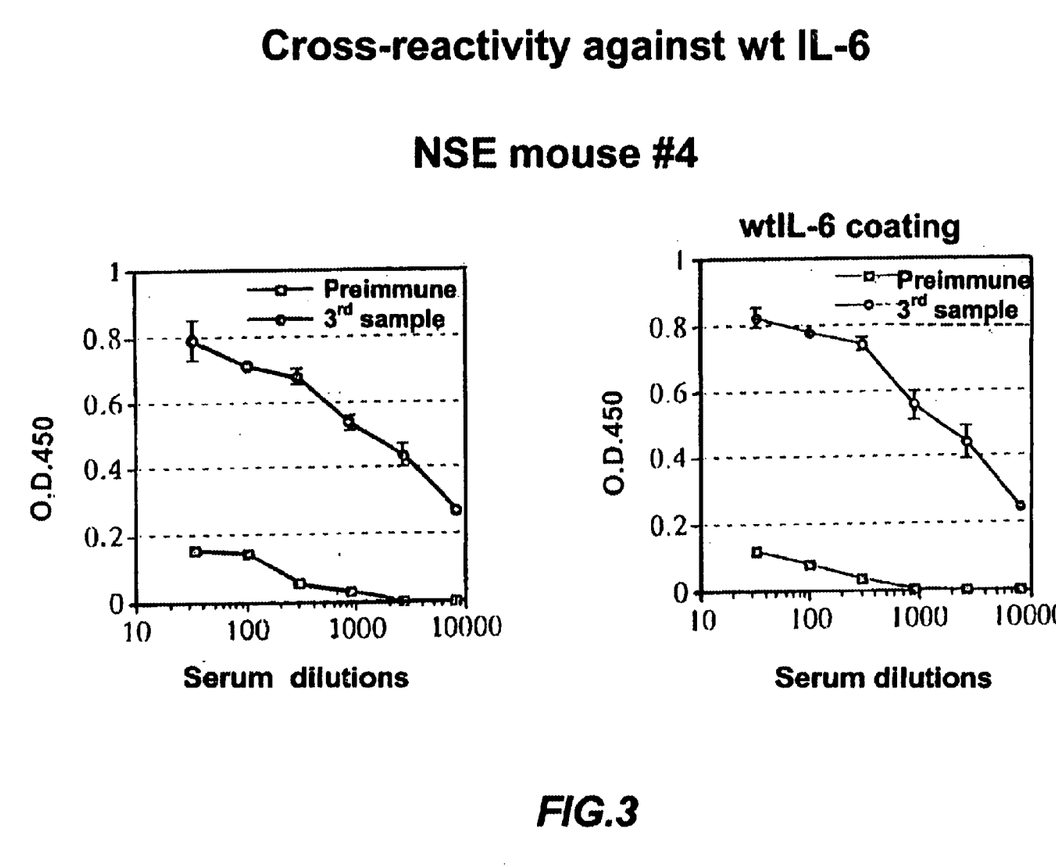
FIG. 3 shows the results of the experiment aimed at verifying whether or not the antibodies developed in mice against Sant1 are also capable of recognising wild-type IL-6.

FIGS. 2a and 2b show the results of the experiment on immunisation using a mutant form of IL-6, Sant1, of a typical normal mouse and of a typical NSE-hIL-6 transgenic mouse, respectively. In this case both the mice developed a large amount of anti-Sant1 antibodies. In fact, it is possible to detect a relatively strong signal even when the serum is diluted to 1:8100. FIGS. 2a and 2b show how the titers of the second and third samples are calculated for the normal mouse and for the transgenic mouse.

Table 1 gives a summary of titer data (calculated as indicated above) for the second and third sample for all the mice innoculated during this experiment.

TABLE 1

IMMUNOGENICITY OF Sant 1

| MICE | SERUM TITER | | |
|---|---|---|---|
| GROUP | 2nd sample | 3rd sample | |
| WT/wtIL-6 | | | |
| 16 | 245 | 5150 | |
| 17 | 1100 | 3900 | |
| 18 | 1250 | 2600 | |
| 19 | 430 | 1600 | |
| 20 | 210 | 1800 | |
| Average | 674 | 3010 | |
| NSE/wtIL-6 | | | |
| 11 | 80 | 92 | |
| 12 | 90 | 215 | |
| 13 | 24 | 155 | |
| 14 | 135 | 135 | |
| 15 | 27 | 54 | |
| Average | 71 | 130 | Ratio of wt mice titer/ NSE mice titer |
| | 9.5 | 23 | |
| WT/Sant1 | | | |
| 6 | 150 | 270 | |
| 7 | 1450 | dead | |
| 8 | 2900 | 3600 | |
| 9 | 1300 | 2700 | |
| 10 | 3300 | 3800 | |
| Average | 1820 | 2600 | |
| NSE/Sant1 | | | |
| 1 | 4000 | 4000 | |
| 2 | 21.5 | 49 | |
| 3 | 1750 | >10000 | |
| 4 | 1750 | 1150 | |
| 5 | 2000 | 1800 | |
| Average | 1900 | 3400 | Ratio of wt mice titer/ |
| | 1 | 0.76 | |

As regards the mice innoculated with the wtIL-6 antigen, it can be seen that, apart from the variations between one animal and another, on average the non-transgenic mice developed an antibody response against wtIL-6 10–20 times stronger than that obtained in the NSE/IL-6 transgenic mice, this being proof of the fact that the transgenic mice have developed an immune tollerance of human hIL-6.

On the contrary, as regards the mice innoculated with the antigen Sant 1, it can be seen that, once again apart from the variations between one animal and another, on average the non-transgenic mice developed an antibody response equivalent to that obtained in NSE/hIL-6 transgenic mice, suggesting that the seven mutations, which when introduced into hIL-6 generated Sant1, have also rendered the mutant Sant1 a completely foreign protein for an immune system that otherwise displays tollerance to hIL-6.

EXAMPLE 2

The Antibodies Developed in the Serum of NSE/hIL-6 Immunized With Sant1 are Capable of Recognising not Only Sant1, but Also Wild-type hIL-6

This was to test whether or not the antibodies developed by mice against Sant1 were capable of recognising not only Sant1 itself, but also wild-type hIL-6 (wt hIL-6). This hypothesis was tested once again using an LISA test. After having verified the fact that antibodies developed in NSE/hIL-6 transgenic mice immunised with Sant1 are capable of recognising and binding the same mutant Sant1 immobilised on the bottom of ELISA plate wells, in a second experiment the wild-type IL-6 was bound in a non-covalent manner to the bottom of ELISA plate wells. After the phase in which the plastic of the wells is saturated with BSA, dilutions of serum from mice immunized with Sant1 were added to the wells to verify whether or not there was a presence of antibodies capable of recognising wtIL-6. For example, FIG. 3 shows the results of the experiment for the NSE/hIL-6 transgenic mouse. As can be seen, the antibody responses obtained for Sant1 and for wild-type IL-6 are. extremely similar. In other words, it is possible to detect the presence of antibodies that have bound the wtIL-6 immobilised on the bottom of the wells in the serum of the third sample, even when the latter is diluted to a ratio of 1:8100. It should be noted that when the NSE/hIL-6 transgenic mice are immunised directly using wild-type IL-6, the antibody response directed at wild-type IL-6 itself is much lower: in effect it is not possible to detect anti-wtIL-6 antibodies in serum diluted to 1:8100 (see FIG. 1). Other NSE/hIL-6 transgenic mice showed a response similar to that of the mouse illustrated in the example.

EXAMPLE 3

The Antibodies Developed in NSE/hIL-6 Immunised With Sant1 are Also Capable of Neutralising the Biological Activity of Wild-type hIL-6

The object was to test whether or not these antibodies, developed in NSE/hIL-6 transgenic mice immunised with Sant1, but capable of recognising wild-type IL-6, are also capable of neutralising the biological activitiy of wild-type IL-6 itself.

The biological activity of wild-type IL-6 under consideration was the ability to stimulate transcription by the C-reactive protein gene promoter in human Hep3B hepatoma cells. The effectiveness of stimulation of transcription was measured according to the state of the art (Gregory, B., Savino, R. and Ciliberto, G., J. Immunological Methods, 170, 47–56, 1994). Human Hep3B hepatoma cells were stimulated with 4 ng/ml of wild-type IL-6, in the presence of serial dilutions of the serum obtained n the third sample from two NSE/hIL-6 transgenic mice #4 and #5 (both immunised with Sant1) The results of the experiment are given in FIG. 4. It can be seen that both the serums diluted to 1:100 almost completely inhibit the biological activity of wild-type hIL-6 at 4 ng/ml on human hepatoma cells.

At this point, investigations were carried out as to whether or not the occurance of this cross-reactive antibody response against wild-type hIL-6 was capable of altering the levels of wild-type hIL-6 measured in the serum of the NSE/hIL-6 transgenic mice immunized with Sant1. The hIL-6 levels were measured according to the state of the art by means of a "sandwich" ELISA test, using a commercially available kit produced by the company "R&D Systems", and scrupulously following the manufacturer's instructions. The levels of hIL-6 found both in the pre-immune sample and in the third sample were measured for four transgenic mice who had been immunized with Sant1. The results are summarised in table 2. As can be seen, immunisation using Sant1, as well as causing the appearance of a strong antibody response that recognises both Sant1 itself and the wtIL-6, also causes an average decrease of over 500 times in the levels of hIL-6 that can be detected in the serum of the NSE/hIL-6 mice using the ELISA "sandwich" kit produced by R&D Systems.

TABLE 2

Decrease in the levels of hIL-6 that can be detected in the serum of NSE/hIL-6 mice

| | hIL-6 levels in the serum | |
|---|---|---|
| | pre-immune serum | 3rd sample |
| Mouse No. 1 | 26 ng/ml | 0.02 ng/ml |
| Mouse No. 2 | 39 ng/ml | 0.01 ng/ml |
| Mouse No. 3 | 28 ng/ml | 0.10 ng/ml |
| Mouse No. 4 | 35 ng/ml | 0.10 ng/ml |
| average | 32 ng/ml | 0.057 ng/ml |

EXAMPLE 4

The Antibodies Developed in NSF/hIL-6 Mice Vaccinated With Sant1 are Able to Neutralize the Biological Activity of Wild-type hIL-6 Also in vivo It is well known that IL-6 induces the production of a series of proteins (called "acute phase proteins") by the liver. Serum Amyloid A, hereon referred as SAA, shows intense and rapid increase during acute events.

The objective was to test whether or not these antibodies, developed in NSE/hIL-6 transgenic mice vaccinated with Sant1, and capable of cross-reacting with wtIL-6, are also capable of neutralising the biological activity of wild type hIL-6 in vivo, measured as inhibition of the increase of mouse SAA (mSAA) following the injection of hIL-6. To this purpose, a blood sample (hereon referred as pre-injection sample) was taken from unimmunised (control) NSE/hIL-6 mice, from wt hIL-6 immunised and from Sant1 immunised NSE/hIL-6 mice. After the animals recovered from the bleeding, they were injected intra-peritoneally with 10 µg of wt hIL-6. Nine hours after the injection, a second blood sample (hereon referred as post-injection sample) was taken from both groups of animals. The mSAA levels were measured both in the pre-injection sample and in the post-injection sample according to the state of the art by means of a "sandwich" ELISA test, using a commercially available kit produced by the company "Biosource International", and scrupulously following the manufacturer's instructions. The results are summarised in Table 3. As can be seen, apart from the variations from between one animal and another, on average in unimmunised mice injection of 10 µg of hIL-6 determined a significant increase in the serum SAA levels, increase which was absent in the Sant1 vaccinated mice injected with the same amount of hIL-6. Therefore, vaccination with Sant1, as well as causing the appearance of a strong antibody response that recognises both Sant1 itself and the wthIL-6 and that is able to neutralize wt hIL-6 biological activity in vitro on human hepatoma cells, prevents in vivo the increase of mSAA levels induced by injection of hIL-6, in other words in neutralizes the biological activity of hIL-6 also in vivo. It should be noticed that immunization with wild type hIL-6, induces the production of a low amount of anti hIL-6 antibodies (see Example 1), and this is not not able to prevent in vivo the increase of mSAA levels induced by injection of hIL-6, because mice immunized with wild type hIL-6 show an increase in the serum SAA levels comparable to the one observed in unimmunised control mice.

TABLE 3

Increase in the levels of mSAA detectable in the serum of Sant1-immunised and control NSE/hIL-6 transgenic mice after hIL-6 injection.

| | | mSAA levels in the serum | | mSAA levels fold increase | |
|---|---|---|---|---|---|
| Mice group | mouse number | pre-inject. sample | post-inject. sample | single mouse | group average |
| Sant1 immunised | 1 | 68 µg/ml | 24 µg/ml | 0.35 | 1.13 |
| | 3 | 23 µg/ml | 14 µg/ml | 0.61 | |
| | 28 | 83 µg/ml | 93 µg/ml | 1.12 | |
| | 36 | 62 µg/ml | 105 µg/ml | 1.7 | |
| | 37 | 95 µg/ml | 177 µg/ml | 1.87 | |
| Control unimmunised | 5 | 112 µg/ml | 718 µg/ml | 6.4 | 9.01 |
| | 8 | 41 µg/ml | 694 µg/ml | 16.9 | |
| | 14 | 140 µg/ml | 613 µg/ml | 4.4 | |
| | 21 | 47 µg/ml | 479 µg/ml | 10.13 | |
| | 22 | 51 µg/ml | 412 µg/ml | 8.1 | |
| | 51 | 53 µg/ml | 433 µg/ml | 8.15 | |
| wt hIL-6 immunised | 11 | 72 µg/ml | 784 pg/ml | 10.3 | 8.9 |
| | 12 | 54 µg/ml | 380 µg/ml | 6.9 | |
| | 13 | 28 µg/ml | 310 g/ml | 11.1 | |
| | 15 | 16 µg/ml | 117 g/ml | 7.2 | |

EXAMPLE 5

Immunisation of NSEhIL-6 Transgenic Mice With hIL-6 and Sant1 Formulated in a Different Adjuvant, Aluminum Hydroxide It is well known that different antigens behaves differently when formulated in different adjuvants (Gupta, R. K. and Siber, G. R., Vaccine, 13, 1263–1276, 1995). The Complete (or Incomplete) Freund Adjuvant used in the immunization experiment described in the Example 1 cannot be used in humans because of side effects, mostly local reactions at the site of injection such as granuloma and cyst formation (Gupta, R. K. and Siber, G. R., Vaccine, 13, 1263–1276, 1995). The objective was to determine whether a similar immune response, with high titer antibodies against Sant1 and also against wt hIL-6 could be raised in NSE/hIL-6 transgenic mice using an adjuvant commonly used for vaccination in humans. For this purpose, aluminum hydroxide was chosen, because it is today the common adjuvant for human use, with an excellent track record of safety (Gupta, R. K. and Siber, G. R., Vaccine, 13, 1263–1276, 1995).

Groups of 8–10 NSE/hIL-6 transgenic mice (plus ten non-transgenic siblings born in the same litters used as controls) were immunized intraperitoneally with 100 µg of antigen (either Sant1 or wild type hIL-6) formulated in aluminum hydroxide at 1 mg/ml in a total volume of 100 µl (100 µg of aluminum hydroxide) for each injection, using an immunization protocol identical to the one described in the Example 1. The second blood sample (taken after the second injection or first booster) and the third blood sample (oaken after the third injection or second booster) were then tested for the presence of antibodies against the antigen used for the immunization by means of the "ELISA" described in the Example 1.

To carry out objective measurements that are comparable for all animals the dilution of serum that gives a reading of 0.5 O.D.$_{450}$ above the highest reading of the preimmune serum from the same animal has been conventionally termed "titer". The titer was measured as illustrated in FIGS. 1a, 1b, 2a and 2b for both normal and transgenic mice immunized with wild type hIL-6 and with Sant1. The results are reported in Table 4.

In general the amount of antibodies against the antigen obtained in this immunization experiment (titer) is higher as compared with the amount of antibodies obtained in the immunization experiment described in Example 1; indeed, it is part of the state of the art the fact that aluminum adjuvants are the adjuvants of choice for induction of serum antibodies (Gupta, R. K. and Siber, G. R., Vaccine, 13, 1263–1276, 199S). More in particular, as regards the mice immunized with the wt hIL-6 antigen, it can be seen again that (apart from the variation from one animal and another) on average the non-transgenic mice developed an antibody response against wt hIL-6 12–18 times stronger than that obtained in NSE/hIL-6 transgenic mice, this being proof of the fact that the transgenic mice have developed an immune tolerance to human IL-6 also when this antigen is injected formulated in aluminum hydroxide as adjuvant. On the contrary, as regards the mice immunized with Sant1 formulated in aluminum hydroxide, it can be seen that also in this case on average the non-transgenic mice developed an antibody response equivalent to that obtained in NSE/hIL-6 transgenic mice, as it was in the immunization experiment described in Example 1, suggesting that the seven mutations (which when introduced into hIL-6 generated Sant1) have rendered the mutant completely foreign protein also when formulated in aluminum hydroxide.

TABLE 4

Immunogenicity of Sant1 and of wt hIL-6 formulated in aluminum hydroxide and injected intraperitoneally and NSE/hIL-6 transgenic and wild type control mice.

| Mice group | mouse number | SERUM TITER | |
|---|---|---|---|
| | | 2$^{nd}$ sample | 3$^{rd}$ sample |
| Non-transgenic mice immunised with wild type hIL-6 in aluminum hydroxide via I.P. | 30 | 21960 | 11848 |
| | 32 | 6070 | 15790 |
| | 34 | 7460 | 46000 |
| | 46 | 14145 | 19600 |
| | 49 | 6240 | 18600 |
| | 54 | 1270 | 6960 |
| | 56 | 218 | 320 |
| | 58 | 5470 | 5260 |
| | 63 | 2138 | 2373 |
| | 65 | 1200 | 3810 |
| Average of the group | | 6617 | 13056 |
| NSE/hIL-6 mice immunised with wild type hIL-6 in aluminum hydroxide via I.P. | 35 | 450 | 530 |
| | 51 | 2200 | 1630 |
| | 53 | 169 | 100 |
| | 60 | 160 | 630 |
| | 75 | 55 | 217 |
| | 85 | 81 | 1440 |
| | 87 | 110 | 176 |
| | 90 | 64 | 390 |
| | 93 | 1900 | 1700 |
| | 99 | 194 | 555 |
| Averages of the group | | 538 | 737 |
| Non-transgenic mice immunised with Sant1 in | 20 | 7270 | 28185 |
| | 21 | 7580 | 30200 |
| | 26 | 3555 | 54330 |
| | 27 | 2185 | 10960 |
| | 28 | 9060 | 35700 |
| | 29 | 7910 | 34515 |

TABLE 4-continued

Immunogenicity of Sant1 and of wt hIL-6 formulated in aluminum hydroxide and injected intraperitoneally and NSE/hIL-6 transgenic and wild type control mice.

| Mice group | mouse number | SERUM TITER | |
|---|---|---|---|
| | | 2$^{nd}$ sample | 3$^{rd}$ sample |
| aluminum hydroxide via I.P. | 33 | 7380 | 43980 |
| | 34 | 1160 | 10550 |
| | 36 | 5785 | 19880 |
| | 43 | 5035 | 23155 |
| Averages of the group | | 5692 | 29145 |
| NSE/hIL-6 mice immunised with Sant1 in aluminun hydroxide via I.P. | 22 | 4520 | 33105 |
| | 35 | 3516 | 28690 |
| | 38 | 9990 | 44680 |
| | 44 | 3580 | 14430 |
| | 46 | 1480 | 9940 |
| | 59 | 9780 | 20525 |
| | 61 | 2360 | 63970 |
| | 79 | 2250 | 26330 |
| Averages of the group | | 4400 | 30210 |

EXAMPLE 6

The Antibodies Developed in the Serum of NSE/hIL-6 Mice Vaccinated With Sant1 Formulated in Aluminum Hydroxide are Capable of Recognising not Only Sant1 but Also Wild-type hIL-6

This was to test whether the antibodies developed against Sant1 in NSE mice vaccinated with Sant1 formulated in aluminum hydroxide were capable of cross-reacting with wild type hIL-6 (wt hIL-6). This was tested once again by "ELISA" using the same methodology described in the Example 2. The antibody titer was calculated as previously described and as illustrated in FIGS. 1a, 1b, 2a and 2b, and the data obtained are reported in Table 5.

TABLE 5

Cross-reactivity against wt hIL-6 of sera of NSE/hIL-6 transgenic mice vaccinated with Sant1 formulated in aluminum hydroxide and injected intraperitoneally.

| Mice group | mouse number | 2$^{nd}$ sample serum titer | | 3$^{rd}$ sample serum titer | |
|---|---|---|---|---|---|
| | | wt hIL-6 | Sant1 | wt hIL-6 | Sant1 |
| NSE/hIL-6 mice vaccinated with Sant1 in aluminun hydroxide via I.P. | 22 | 2525 | 4520 | 31180 | 33105 |
| | 35 | 1925 | 3516 | 11860 | 28690 |
| | 38 | 7065 | 9990 | 43850 | 44680 |
| | 44 | 3580 | 3580 | 10585 | 14430 |
| | 46 | 1480 | 1480 | 8675 | 9940 |
| | 59 | 9990 | 9780 | 20360 | 20525 |
| | 61 | 2800 | 2360 | 52000 | 63970 |
| | 79 | 1980 | 2250 | 14890 | 26330 |
| Averages of the group | | 3630 | 4400 | 22800 | 28750 |

Again, also when aluminum hydroxide is used as adjuvant for the immunization, the antibody titers against Sant1 and wild type hIL-6 are similar. Again, it should be noticed that when the NSE/hIL-6 transgenic mice are immunised with wild type hIL-6, the antibody response directed against wild type hIL-6 itself is much lower: for instance in the third blood sample the average titer against wt hIL-6 is 737 in the group of NSE/hIL-6 mice immunised with wt hIL-6 (see Example 5) as compared with an average titer against wt hIL-6 of 22800 (13 times higher) in the group of NSE/hIL-6 mice vaccinated with Sant1.

EXAMPLE 7

The Antibodies Developed in NSE/hIL-6 Mice Vaccinated With Sant1 Formulated in Aluminum Hydroxide are Also Able to Neutralize the Biological Activity of Wild Type hIL-6

The objective was to test whether or not these antibodies, developed in NSE/hIL-6 transgenic mice vaccinated with Sant1 formulated in aluminum hydroxide, but capable of recognising wild type hIL-6, are also capable of neutralising the biological activity of wild type hIL-6 itself.

Figure 4:
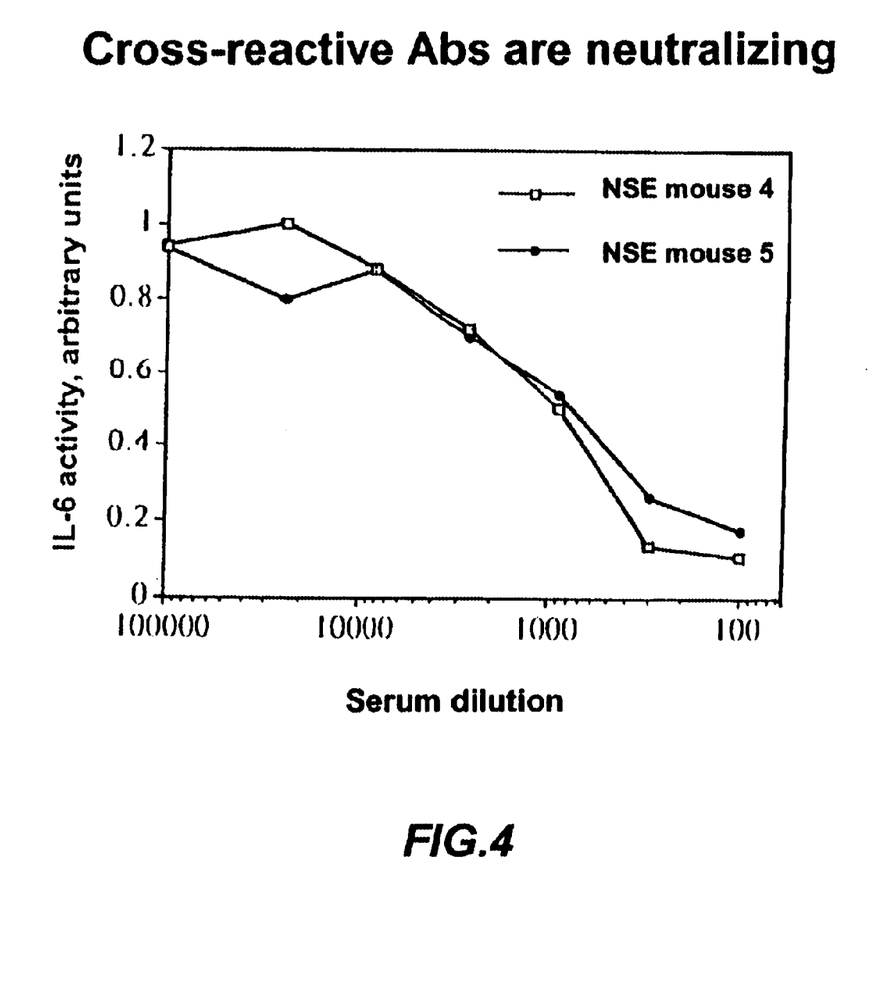
FIG. 4 shows the results of the experiment aimed at verifying whether or not the antibodies developed in NSE/hIL-6 transgenic mice immunised with the wild-type interleukin 6 mutant Sant1 are capable of neutralising the biological activity of wild-type human interleukin 6.
Figure 5A:
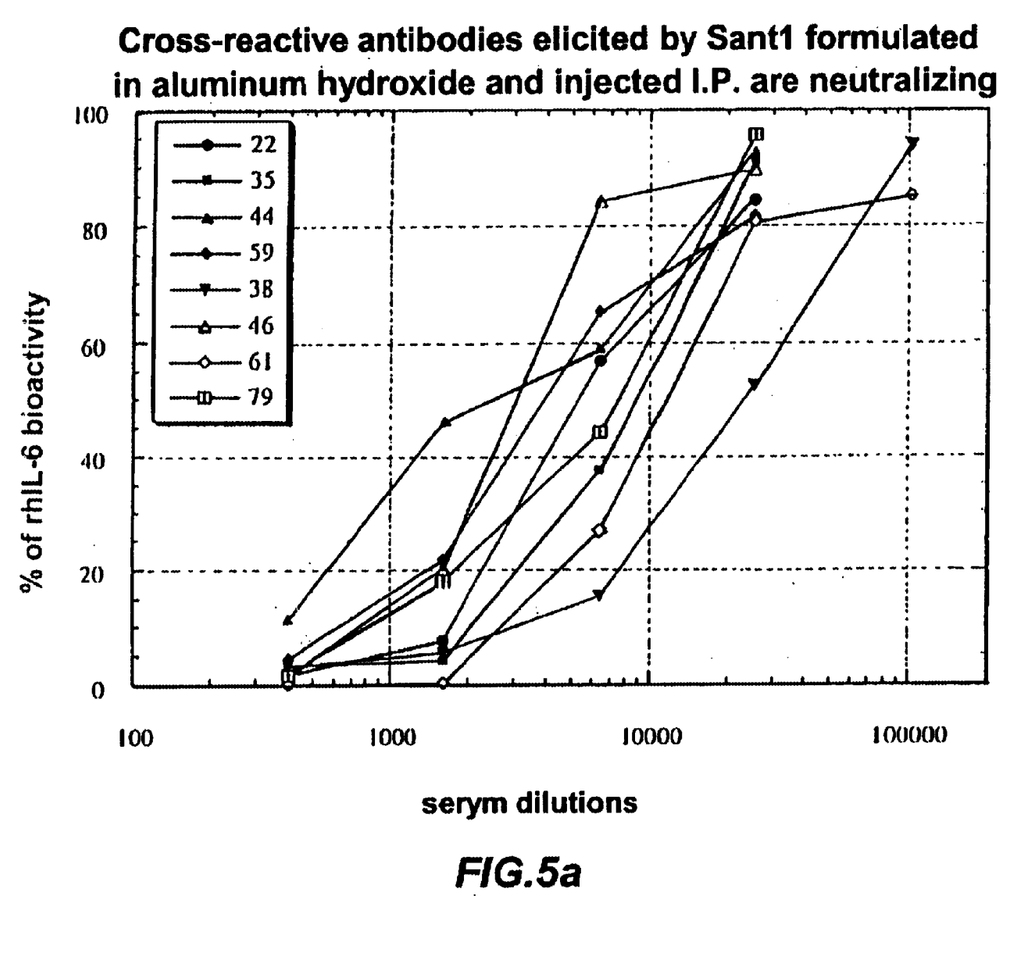
FIGS. 5a and 5b show the results of experiments carried out in example 7.
Figure 5B:
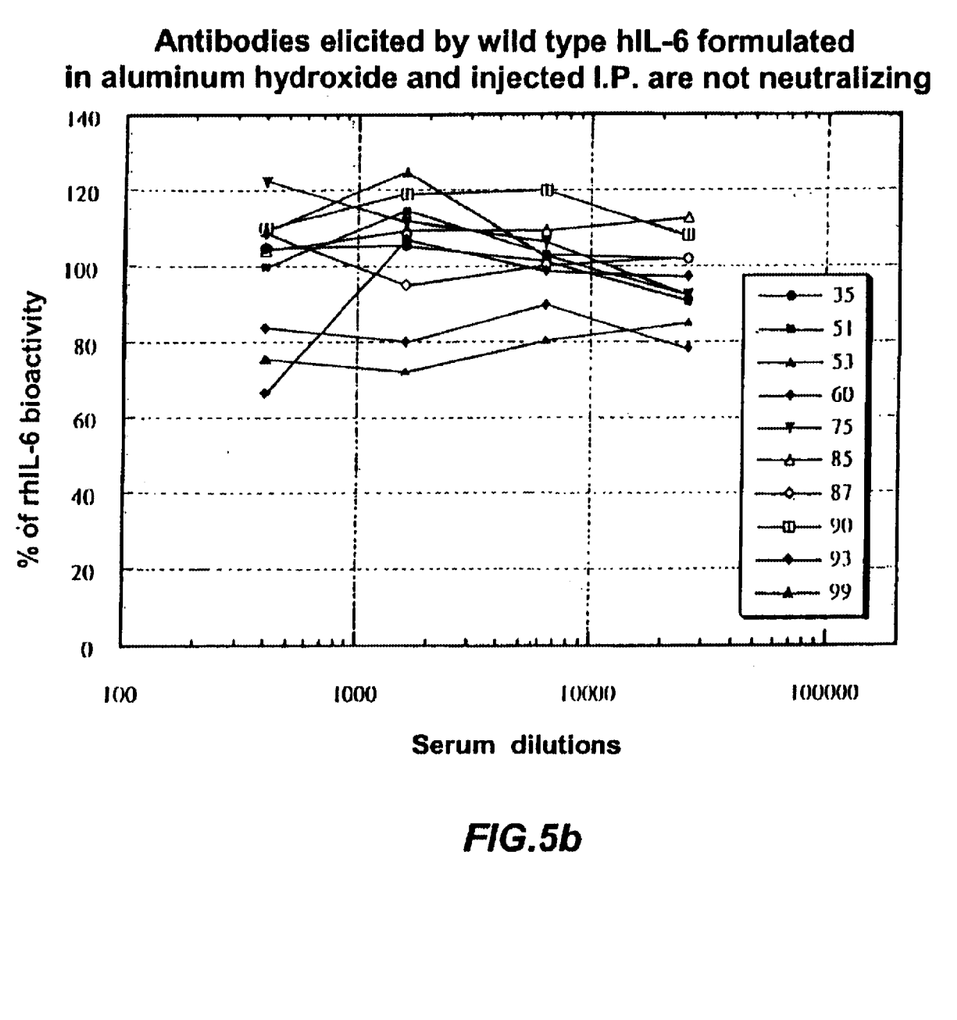

The biological activity of wild-type IL-6 under consideration was the ability to stimulate transcription by the C-reactive gene promoter in human Hep3B hepatoma cells. The effectiveness of transcriptional stimulation was measured according to the state of the art (Gregory, B., Savino, R. and Ciliberto, G., *J. Immunological Methods*, 170, 47–56, 1994). Human Hep3B hepatoma cells were stimulated with 4 ng/ml of wild-type hIL-6, and this extent of stimulation was taken as 100%, or with 4 ng/ml of wild type hIL-6 in the presence of serial dilutions of the serum obtained from the third blood sample from NSE/hIL-6 mice immunised with both Sant1 and wild type hIL-6; in the latter cases the extent of transcriptional stimulation was expressed as percent of the stimulation obtained in cells incubated with 4 ng/ml of wild type hIL-6 only. The results of the experiment are given in FIGS. 5a and 5b. It can be seen that the serum of all mice diluted 1:400 almost completely inhibits the biological activity of wild type hIL-6 at 4 ng/ml on human hepatoma cells. Therefore, the ability to neutralize the bioactivity of exogenously added hIL-6 on human hepatoma cells was even higher for the sera of animals immunized with aluminum hydroxide than in the case of animals immunized with CFA (see Example 3 and compare FIG. 5a with FIG. 4) When NSE/hIL-6 transgenic mice are immunised with wild type hIL-6 the very low amount of anti hIL-6 antibodies obtained is not sufficient to inhibit wild type hIL-6 biological activity on human hepatoma cells (see FIG. 5b).

Also in this case, investigations were carried out as to whether or not the occurrance of this cross-reactive immune response against wild type hIL-6 was capable of altering the levels of wild type hIL-6 measured in the serum of NSE/hIL-6 transgenic mice immunised with both Sant1 and wild type hIL-6. The hIL-6 levels were measured as described in the Example 3 both in the pre-immune sample and in the third sample of both groups of mice. The results are summarised in Table 6. As can be seen, vaccination using Sant1 formulated in aluminum hydroxide, as well as causing the appearance of a strong antibody response that recognises both Sant1 itself and the wild type hIL-6, also causes an average decrease of about 1,400 times in the levels of hIL-6 that can be detected in the serum of the NSE/hIL-6 transgenic mice. Immunisation using wild type hIL-6 itself formulated in the same adjuvant causes only a marginal decrease (3-fold as compared with 1,400-fold) in the levels of hIL-6 that can be detected in the serum.

TABLE 6

Decrease in the levels of hIL-6 that can be detected in the serum of NSE/hIL-6 mice immunised with Sant1 and wt hIL-6 formulated in aluminum hydroxide.

| Mice | mouse | hIL-6 levels in the serum (pg/ml) | |
|---|---|---|---|
| group | number | Pre-immune sample | 3$^{rd}$ sample |
| NSE/hIL-6 | 35 | 27505 pg/ml | 3522 pg/ml |
| mice | 51 | 24950 pg/ml | 2662 pg/ml |
| immunised | 53 | 25817 pg/ml | 4566 pg/ml |
| with | 60 | 23283 pg/ml | 9810 pg/ml |
| wild type | 75 | 26373 pg/ml | 8186 pg/ml |
| hIL-6 in | 85 | 23000 pg/ml | 8959 pg/ml |
| aluminum | 87 | 25527 pg/ml | 9172 pg/ml |
| hydroxide | 90 | 25590 pg/ml | 20041 pg/ml |
| via | 93 | 23275 pg/ml | 5834 pg/ml |
| I.P. | 99 | 30830 pg/ml | 6582 pg/ml |
| Averages of the group | | 25585 pg/ml | 7933 pg/ml |
| NSE/hIL-6 | 22 | 27300 pg/ml | *9 pg/ml |
| mice | 35 | 31778 pg/ml | *9 pg/ml |
| immunised | 38 | 25223 pg/ml | *9 pg/ml |
| with | 44 | 29385 pg/ml | 41 pg/ml |
| Sant1 in | 46 | 20600 pg/ml | *9 pg/ml |
| aluminum | 59 | 22820 pg/ml | 45 pg/ml |
| hydroxide | 61 | 23125 pg/ml | *9 pg/ml |
| via I.P. | 79 | 24510 pg/ml | *9 pg/ml |
| Averages of the group | | 25593 pg/ml | 18 pg/ml |

The star (*) indicates the lower limit of sensitivity of the assay.

EXAMPLE 8

The Antibodies Developed in NSE/hIL-6 Mice Vaccinated With Sant1 Formulated in Aluminum Hydroxide are Able to Neutralize the Biological Activity of wt hIL-6 Also in vivo The objective was to test whether or not these, antibodies, developed in NSE/hIL-6 transgenic mice vaccinated with Sant1 formulated in aluminum hydroxide, but capable of recognising wtIL-6, are also capable of neutralising the biological activity of wild type hIL-6 in vivo, measured as the increase of mouse SAA (mSAA) serum levels induced in the mice by injection of hIL-6, as described in the Example 4. The experiment was performed as described in the Example 4 on unimmunised (control) NSE/hIL-6 mice and on NSE/hIL-6 mice immunized with Sant1 formulated in aluminum hydroxide. The results are summarised in Table 7. As can be seen, apart from the variations from between one animal and another, on average again in unimmunized mice injection of 10 μg of hIL-6 determined a 5- to 6-fold increase in the serum SAA levels. No increase was obtained in the mice vaccinated with Sant1 formulated in aluminum hydroxide, injected with the same amount of hIL-6.

TABLE 7

Increase in the levels of mSAA detectable in the serum of Sant1-vaccinated and control NSE/hIL-6 transgenic mice after hIL-6 injection.

| | | mSAA levels in the serum | | mSAA levels fold increase | |
|---|---|---|---|---|---|
| Mice group | mouse number | pre-inject. sample | post-inject. sample | single mouse | group average |
| Sant1 vaccinated | 22 | 6.1 μg/ml | 7.1 μg/ml | 1.14 | 1.19 |
| | 35 | 4.4 μg/ml | 5.5 μg/ml | 1.24 | |
| | 38 | 7.4 μg/ml | 9.9 μg/ml | 1.34 | |
| | 44 | 4.6 μg/ml | 6.5 μg/ml | 1.4 | |

TABLE 7-continued

Increase in the levels of mSAA detectable in the serum of Sant1-vaccinated and control NSE/hIL-6 transgenic mice after hIL-6 injection.

| Mice group | mouse number | mSAA levels in the serum | | mSAA levels fold increase | |
|---|---|---|---|---|---|
| | | pre-inject. sample | post-inject. sample | single mouse | group average |
| | 46 | 5.2 μg/ml | 6.9 μg/ml | 1.33 | |
| | 59 | 6.7 μg/ml | 7.5 μg/ml | 1.13 | |
| | 61 | 8.6 μg/ml | 10.2 μg/ml | 1.19 | |
| | 79 | 8.8 μg/ml | 6.8 μg/ml | 0.77 | |
| Control unimmunised | 15 | 85 μg/ml | 265 μg/ml | 3.1 | 5.41 |
| | 16 | 99 μg/ml | 366 μg/ml | 3.7 | |
| | 19 | 296 μg/ml | 2997 μg/ml | 10.1 | |
| | 20 | 41 μg/ml | 146 μg/ml | 3.6 | |
| | 21 bis | 45 μg/ml | 276 μg/ml | 6.1 | |
| | 55 | 41 μg/ml | 303 μg/ml | 7.4 | |
| | 56 | 75 μg/ml | 291 μg/ml | 3.9 | |

Therefore, vaccination with Sant1, as well as causing the appearance of a strong antibody response that recognises both Sant1 itself and the wthIL-6 and that is able to neutralize wt hIL-6 biological activity in vitro on human hepatoma cells, prevents in vivo the increase of mSAA levels induced by injection of hIL-6, in other words in neutralizes the biological activity of hIL-6 also in vivo.

EXAMPLE 9

Vaccination of NSEhIL-6 Transgenic Mice With hIL-6 and Sant1 Formulated in aluminum Hydroxide via Intradermal Administration Route Examples 5, 6, 7 and 8 above show that it is possible to obtain in animals otherwise tolerant to wt hIL-6 a strong antibody response against wt hIL-6 itself, that is able to neutralize hIL-6 bioactivity both in vitro and in vivo, by using a mutant form of hIL-6 (Sant1) formulated in an adjuvant (aluminum hydroxide) compatible with human use. However, in the immunisation experiment described in the Example 5, the antigen was injected intraperitoneally, which is not an administration route commonly used for immunization in humans. The objective was to determine whether a similar immune response, with high titer antibodies against Sant1 and also against wt hIL-6 could be raised in NSE/hIL-6 transgenic mice using an administration route used for vaccination in humans.

Groups of 8–9 NSE/hIL-6 transgenic mice (plus ten non-transgenic siblings born in the same litters used as controls) were immunised intradermally (I.D.), an administration route in mouse which correspond to the subcutaneous (S.C.) administration route in humans, currently used for the administration of several vaccines as described in the state of the art. Again, 100 μg of antigen (either Sant1 or wild type hIL-6) formulated in aluminum hydroxide at 1 mg/ml in a total volume of 100 μl (100 μg of aluminum hydroxide) were used for each injection, using an immunization protocol identical to the one described in the Example 1. The second blood sample (taken after the second injection or first booster) and the third blood sample (taken after the third injection or second booster) were then tested for the presence to antibodies against the antigen used for the immunization by means of an "ELISA" method identical to the one already described in the Example 1.

To carry out objective measurements that are comparable for all animals the dilution of serum that gives a reading of 0.5 O.D.$_{450}$ above the highest reading of the preimmune serum from the same animal has been conventionally termed "titer". The titer was measures as illustrated in FIGS. 1a, 1b, 2a and 2b for both normal and transgenic mice immunized with wild type hIL-6 and with Sant1. The results are reported in Table 8.

Again, as regards the mice immunized with the wt hIL-6 antigen, it can be seen again that (apart from the variation from one animal and another) on average the non-transgenic mice developed an antibody response against wt hIL-6 40–50 times stronger than that obtained in NSE/hIL-6 transgenic mice, this being proof of the fact that the transgenic mice have developed an immune tolerance to human IL-6 also when this antigen is injected formulated in aluminum hydroxide via intradermal administration route. On the contrary, as regards the mice immunized with Sant1 formulated in aluminum hydroxide, it can be seen that also in this case on average the non-transgenic mice developed an antibody response equivalent to that obtained in NSE/hIL-6 transgenic mice, as it was in the immunization experiments described in Example 1 and 5, suggesting that the seven substitutions (which when introduced into hIL-6 generated Sant1) have rendered the mutant a completely foreign protein also when formulated in aluminum hydroxide and injected via intradermal administration route.

TABLE 8

Immunogenicity of Sant1 and of wt hIL-6 formulated in aluminum hydroxide and injected intradermally (I.D.) and NSE/hIL-6 transgenic and wild type control mice.

| Mice group | mouse number | SERUM TITER | |
|---|---|---|---|
| | | 2$^{nd}$ sample | 3$^{rd}$ sample |
| Non-transgenic | 31 | 6220 | 4250 |
| mice | 45 | 888 | 1270 |
| immunised | 48 | 52 | 1150 |
| with | 50 | 1060 | 7640 |
| wild type | 55 | 4050 | 4560 |
| hIL-6 in | 57 | 4337 | 9260 |
| aluminum | 61 | 4065 | 9020 |
| hydroxide | 64 | 13690 | 20000 |
| via | 66 | 5460 | 7500 |
| I.D. | 65 | 680 | 700 |
| Averages of the group | | 4050 | 6535 |
| NSE/hIL-6 | 47 | 240 | 195 |
| mice | 52 | 51 | 25 |
| immunised | 62 | 30 | 120 |
| with | 81 | 39 | 160 |
| wt hIL-6 | 86 | 97 | 200 |
| in aluminum | 91 | 77 | 100 |
| hydroxide | 96 | 306 | 210 |
| via I.D. | 2 | 25 | 100 |
| Averages of the group | | 108 | 139 |
| | 25 | 890 | 4610 |
| Non-transgenic | 30 | 540 | 3670 |
| mice | 31 | 4370 | 13960 |
| immunised | 32 | 1770 | 10690 |
| with | 37 | 7860 | 13235 |
| Sant1 in | 39 | 8400 | 26680 |
| aluminum | 40 | 7360 | 49774 |
| hydroxide | 45 | 6510 | 4770 |
| via I.D. | 50 | 1000 | 16280 |
| | 53 | 470 | 3100 |
| Averages of the group | | 3920 | 14680 |
| | 41 | 4640 | 5735 |
| NSE/hIL-6 | 42 | 2145 | 7640 |
| mice | 47 | 1150 | 4490 |
| immunised | 48 | 1600 | 8700 |
| with | 49 | 2110 | 6740 |
| Sant1 in | 51 | 8980 | 20250 |
| aluminum | 52 | 11400 | 23380 |

TABLE 8-continued

Immunogenicity of Sant1 and of wt hIL-6
formulated in aluminum hydroxide and
injected intradermally (I.D.) and NSE/hIL-6
transgenic and wild type control mice.

| Mice | mouse | SERUM TITER | |
|---|---|---|---|
| group | number | 2nd sample | 3rd sample |
| hydroxide | 36 | 2030 | 9880 |
| via I.D. | 65 | 4290 | 14080 |
| Averages of the group | | 4260 | 11210 |

EXAMPLE 10

The Antibodies Developed in the Serum of NSE/hIL-6 Mice Vaccinated With Sant1 Formulated in Aluminum Hydroxide are Capable of Recognising not Only Sant1 but Also Wild-type hIL-6

This was to test whether or not the antibodies developed in NSE mice vaccinated with Sant1 formulated in aluminum hydroxide and injected via intradermal administration route were capable of cross-reacting with wild type hIL-6 (wt hIL-6). This was tested once again by "ELISA" using the same methodology described in the Example 2. The antibody titer was calculated as previously described and as illustrated in FIGS. 1a, 1b, 2a and 2b, and the data obtained are reported in Table 9.

TABLE 9

Cross-reactivity against wt hIL-6 of sera of
NSE/hIL-6 transgenic mice vaccinated with Sant1
formulated in aluminum hydroxide and injected intradermally.

| Mice | mouse | 2nd sample serum titer | | 3rd sample serum titer | |
|---|---|---|---|---|---|
| group | number | wt hIL-6 | Sant1 | wt hIL-6 | Sant1 |
| | 41 | 960 | 4640 | 5800 | 5735 |
| NSE/hIL-6 | 42 | 2720 | 2145 | 7820 | 7640 |
| mice | 47 | 665 | 1150 | 2190 | 4490 |
| vaccinated | 48 | 1010 | 1600 | 7075 | 8700 |
| with | 49 | 2660 | 2110 | 5060 | 6740 |
| Sant1 in | 51 | 6660 | 8980 | 17970 | 20250 |
| aluminun | 52 | 13380 | 11400 | 20740 | 23380 |
| hydroxide | 56 | 2360 | 2030 | 7240 | 9880 |
| via I.D. | 65 | 4290 | 4290 | 10700 | 14080 |
| Averages of the group | | 3656 | 4260 | 9400 | 11210 |

Again, also when aluminum hydroxide is used as adjuvant for the immunization this time via intradermal administration route, the antibody titers against Sant1 and wild type hIL-6 are extremely similar. Once more, it should be noticed that when the NSE/hIL-6 transgenic mice are immunised with wild type hIL-6, the antibody response directed against wild type hIL-6 itself is much lower: for instance in the third blood sample the average titer against wt hIL-6 is 139 in the group of NSE/hIL-6 mice immunised with wt hIL-6 (see Example 9) as compared with an average titer against wt hIL-6 of 9400 (70 times higher) in the group of NSE/hIL-6 mice immunised with Sant1.

EXAMPLE 11

The Antibodies Developed in NSE/hIL-6 Mice Vaccinated With Sant1 Formulated in Aluminum Hydroxide and Injected Intradermally are Also Able to Neutralise the Biological Activity of Wild Type hIL-6

The objective was to test whether or not these antibodies, developed in NSE/hIL-6 transgenic mice vaccinated with Sant1 formulated in aluminum hydroxide and injected intradermally, are also capable of neutralising the biological activity of wild type hIL-6 itself.

Figure 6A:
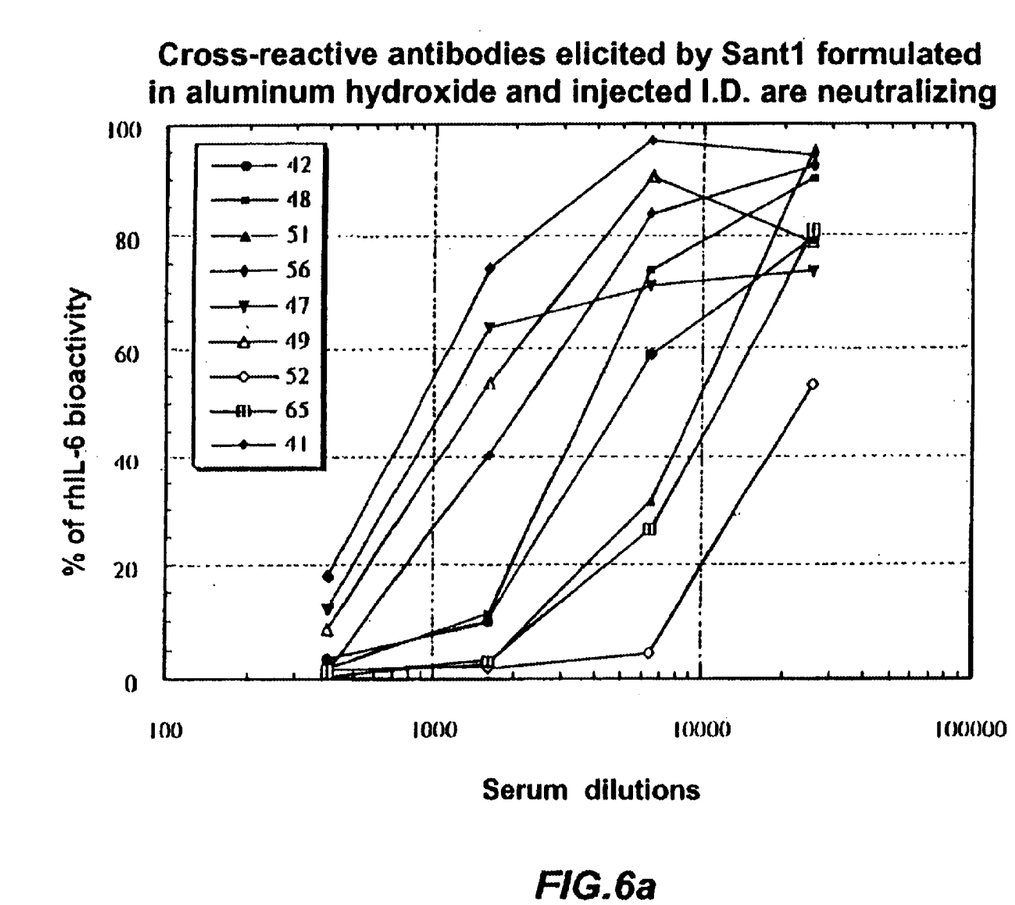
FIGS. 6a and 6b show the results of experiments carried out in example 11.
Figure 6B:
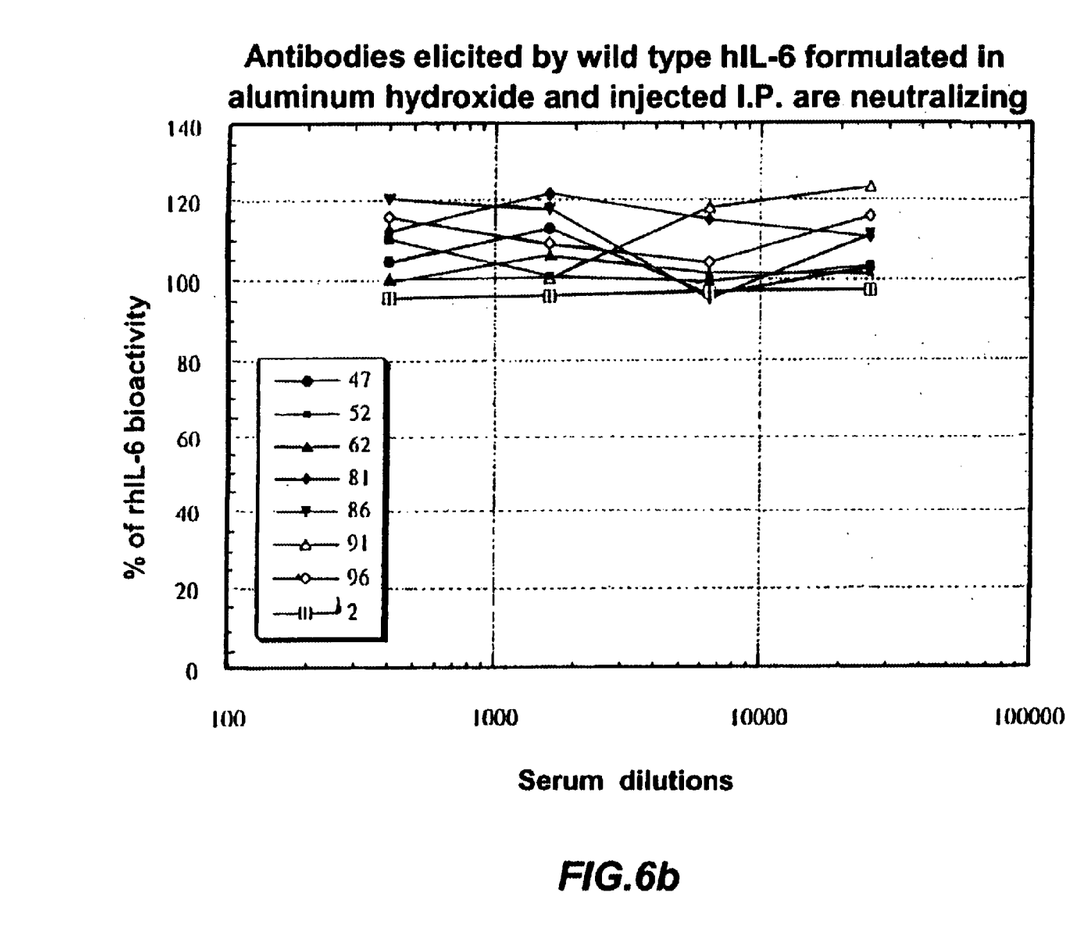

Again, the biological activity of wild-type IL-6 under consideration was the ability to stimulate transcription by the C-reactive gene promoter in human Hep3B hepatoma cells. The effectiveness of transcriptional stimulation was measured according to the state of the art (Gregory, B., Savino, R. and Ciliberto, G., *J. Immunological Methods*, 170, 47–56, 1994). As it was in the Example 7 human Hep3B hepatoma cells were stimulated with 4 ng/ml of wild-type hIL-6, and this extent of stimulation was taken as 100%, or with 4 ng/ml of wild type hIL-6 in the presence of serial dilutions of the serum obtained from the third blood sample from NSE/hIL-6 mice immunised intradermally with both Sant1 and wild type hIL-6; in the letter cases the extent of transcriptional stimulation was expressed as percent of the stimulation obtained in cells incubated with 4 ng/ml of wild type hIL-6 only. The results of the experiment are given in FIGS. 6a and 6b. It can be seen that the serum of all mice diluted 1:400 inhibits more than 80% of the biological activity of wild type hIL-6 at 4 ng/ml on human hepatoma cells. Again, it should be noticed that when NSE/hIL-6 transgenic mice are immunised with wild type hIL-6 the very low amount of anti hIL-6 antibodies obtained is not sufficient to inhibit wild type hIL-6 biological activity on Human hepatoma cells (see FIG. 6b).

Also in this case, investigations were carried out as to whether or not the occurrance of this cross-reactive immune response against wild type hIL-6 was capable of altering the levels of wild type hIL-6 measured in the serum of NSE/hIL-6 transgenic mice immunised with both Sant1 and wild type hIL-6. The hIL-6 levels were measured as described in the Example 3 both in the pre-immune sample and in the third sample of both groups of mice. The results are summarised in Table 10. As can be seen, vaccination using Sant1 formulated in aluminum hydroxide and injected intradermally, as well as causing the appearance of a strong antibody response that recognises both Sant1 itself and the wild type hIL-6, also causes an average decrease of about 350 times in the levels of hIL-6 that can be detected in the serum of the NSE/hIL-6 transgenic mice. On the contrary, immunisation using wild type hIL-6 itself formulated in the same adjuvant causes only a marginal decrease (2.4-fold as compared with 350-fold) in the levels of hIL-6 that can be detected in the serum.

TABLE 10

Decrease in the levels of hIL-6 that can be
detected in the serum of NSE/hIL-6 mice
immunised with Sant1 and wt hIL-6 formulated
in aluminum hydroxide and injected intradermally.

| Mice | mouse | IL-6 levels in the serum ($\mu$g/ml) | |
|---|---|---|---|
| group | number | Pre-immune sample | 3rd sample |
| NSE/hIL-6 | 47 | 23790 pg/ml | 5684 pg/ml |
| mice | 52 | 25450 pg/ml | 3110 pg/ml |
| immunised | 62 | 26190 pg/ml | 4490 pg/ml |
| with | 81 | 24690 pg/ml | 25930 pg/ml |
| wt hIL-6 | 86 | 22890 pg/ml | 8600 pg/ml |
| in aluminum | 91 | 16600 pg/ml | 6884 pg/ml |

TABLE 10-continued

Decrease in the levels of hIL-6 that can be detected in the serum of NSE/hIL-6 mice immunised with Sant1 and wt hIL-6 formulated in aluminum hydroxide and injected intradermally.

| Mice group | mouse number | IL-6 levels in the serum (µg/ml) | |
|---|---|---|---|
| | | Pre-immune sample | 3rd sample |
| hydroxide | 96 | 16760 pg/ml | 5800 pg/ml |
| via I.D. | 2 | 22970 pg/ml | 14670 pg/ml |
| Averages of the group | | 22418 pg/ml | 9396 pg/ml |
| NSE/hIL-6 | 41 | 21640 pg/ml | *9 pg/ml |
| mice | 42 | 19040 pg/ml | *9 pg/ml |
| immunised | 47 | 22940 pg/ml | 173 pg/ml |
| with | 48 | 23990 pg/ml | *9 pg/ml |
| Sant1 in | 49 | 21640 pg/ml | 79 pg/ml |
| aluminun | 51 | 25680 pg/ml | 21 pg/ml |
| hydroxide | 52 | 24410 pg/ml | 17 pg/ml |
| via I.D. | 56 | 26540 pg/ml | 204 pg/ml |
| | 65 | 20410 pg/ml | 78 pg/ml |
| Averages of the group | | 22920 pg/ml | 66 pg/ml |

The star (*) indicates the lower limit of sensitivity of the assay.

EXAMPLE 12

The Antibodies Developed in NSE/hIL-6 Mice Vaccinated With Sant1 Formulated in Aluminum Hydroxide and Injected Intradermally are Able to Neutralize the Biological Activity of wt hIL-6 Also in vivo The objective was to test whether or not these antibodies, developed in NSE/hIL-6 transgenic mice vaccinated with Sant1 formulated in aluminum hydroxide and injected intradermally, are also capable of neutralising one of the biological activities of wild type hIL-6 in vivo, that is the increase of mouse SAA (mSAA) levels normally induced in the mice by injection of hIL-6, as described in the Example 4. The experiment was performed as described in the Example 4 on NSE/hIL-6 mice vaccinated with Sant1 formulated in aluminum hydroxide and injected intradermally. The values obtained have been compared with the control unimmunised mice of the experiments described in the Examples 4 (Table 3) and 8 (Table 7). The results are summarised in Table 11. As can be seen, apart from the variations from between one animal and another, on average again the 7-fold increase in SAA levels caused by hIL-6 injection in unimmunised mice was absent in the mice vaccinated with Sant1 formulated in aluminum hydroxide injected intradermally.

TABLE 11

Increase in the levels of mSAA detectable in the serum of Sant1-immunised and control NSE/hIL-6 transgenic mice after hIL-6 injection.

| Mice group | mouse number | mSAA levels in the serum | | mSAA levels fold increase | |
|---|---|---|---|---|---|
| | | pre-inject. sample | post-inject. sample | single mouse | group average |
| Sant1 vaccinated | 41 | 49 µg/ml | 20 µg/ml | 0.46 | 1.22 |
| | 42 | 10 µg/ml | 9 µg/ml | 0.9 | |
| | 47 | 64 µg/ml | 56 µg/ml | 0.87 | |
| | 48 | 31 µg/ml | 18 µg/ml | 0.74 | |
| | 49 | 8 µg/ml | 18 µg/ml | 2.2 | |
| | 51 | 23 µg/ml | 23 µg/ml | 1.0 | |
| | 52 | 23 µg/ml | 40 µg/ml | 1.7 | |
| | 56 | 39 µg/ml | 41 µg/ml | 1.05 | |
| | 65 | 31 µg/ml | 66 µg/ml | 2.1 | |
| Control unimmunised | 5 | 112 µg/ml | 718 µg/ml | 6.4 | 7.07 |
| | 8 | 41 µg/ml | 694 µg/ml | 16.9 | |
| | 14 | 140 µg/ml | 613 µg/ml | 4.4 | |
| | 15 | 85 µg/ml | 265 µg/ml | 3.1 | |
| | 16 | 99 µg/ml | 366 µg/ml | 3.7 | |
| | 19 | 296 µg/ml | 2997 µg/ml | 10.1 | |
| | 20 | 41 µg/ml | 146 µg/ml | 3.6 | |
| | 21 | 47 µg/ml | 479 µg/ml | 10.13 | |
| | 21 bis | 45 µg/ml | 276 µg/ml | 6.1 | |
| | 22 | 51 µg/ml | 412 µg/ml | 8.1 | |
| | 51 | 53 µg/ml | 433 µg/ml | 8.15 | |
| | 55 | 41 µg/ml | 303 µg/ml | 7.4 | |
| | 56 | 75 µg/ml | 291 µg/ml | 3.9 | |

Therefore, vaccination with Sant1 performed with an adjuvant and an administration route compatible with use in humans, as well as causing the appearance of a strong antibody response that recognises both Sant1 itself and the wthIL-6 and that is able to neutralize wt hIL-6 biological activity in vitro on human hepatoma cells, prevents in vivo the increase of mSAA levels induced by injection of hIL-6, in other words in neutralizes the biological activity of hIL-6 also in vivo.

What is claimed is:

1. A composition comprising an immunologically effective amount of a mutein of wild-type human interleukin-6 (hIL-6) comprising the mutations Tyr31Asp, Gly35Phe, Ser118Arg, Val121Asp, Gln175Ile, Ser176Arg, Gln183Ala, wherein said mutein is:

a) a receptor antagonist of IL-6; and b) an immunogen which, upon vaccination of a recipient, elicits production of antibodies that cross-react with endogenous IL-6 cytokine produced by said recipient.

2. The composition according to claim 1, additionally comprising pharmaceutically acceptable carrier, diluents, excipients or vehicles.

3. The composition according to claim 1, formulated for administration to a recipient as an injectable composition to treat over-production of IL-6 by said recipient, and pathologies related to said over-production of IL-6, said composition additionally comprising pharmaceutically acceptable diluents, excipients, or vehicles.

4. The composition according to claim 3, formulated as an injectable composition to treat over-production of human IL-6 in a recipient, the over-production causing or related to pathologies selected from the group consisting of post-menopausal osteoporosis and cancer cachexy.

5. The composition according to claim 1, wherein said mutein is present in said composition at between about 0.1 to about 100 micrograms per milliliter.

6. The composition according to claim 1, wherein said composition is formulated with aluminum hydroxide at about 1 mg/mL.

7. The composition according to claim 4, wherein said composition is formulated for subcutaneous injection into a recipient.

8. The composition according to claim 7, wherein said composition is formulated for administration to the recipient in three doses.

9. The composition according to claim 1, comprising a mutant of human interleukin-6 (hIL-6) having the same three-dimensional conformation as the mutein identified as Sant 1, the Sant 1 mutein consisting of the seven amino acid substitutions Tyr31Asp, Gly35Phe, Ser118Arg, Val121Asp, Gln175Ile, Ser176Arg, Gln183Ala in the amino acid sequence of wild-type hIL-6.

10. A method of treating post-menopausal osteoporosis and cancer cachexy in a recipient caused by or related to overproduction of IL-6 by said recipient, comprising: administering to said recipient an effective amount of the composition according to claim 1.

11. The method according to claim 10, wherein the administering comprises injection of the composition to induce an immune response effective to reduce the level of endogenous IL-6 in said recipient.

12. A process for the preparation of the composition of claim 1, comprising the step of admixing a mutein of wild-type IL-6 containing the mutations Tyr31Asp, Gly35Phe, Ser118Arg, Val121Asp, Gln175Ile, Ser176Arg, Gln183Ala with pharmaceutically acceptable diluents, excipients or vehicles.

* * * * *